(12) United States Patent
Lin et al.

(10) Patent No.: US 10,066,208 B2
(45) Date of Patent: Sep. 4, 2018

(54) KIT AND METHOD FOR PROMOTING MESENCHYMAL STEM CELL DIFFERENTIATION

(71) Applicant: NATIONAL TAIWAN UNIVERSITY, Taipei (TW)

(72) Inventors: Feng-Huei Lin, Taipei (TW); Jui-Sheng Sun, Taipei (TW); Chunching Li, New Taipei (TW); Ching-Yun Chen, New Taipei (TW); Cherng-Jyh Ke, New Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/700,173

(22) Filed: Apr. 30, 2015

(65) Prior Publication Data

US 2016/0145574 A1 May 26, 2016

(30) Foreign Application Priority Data

Nov. 20, 2014 (TW) .............................. 103140322 A

(51) Int. Cl.
*C12N 5/077* (2010.01)
*C12N 5/0775* (2010.01)

(52) U.S. Cl.
CPC .......... *C12N 5/0655* (2013.01); *C12N 5/0662* (2013.01); *C12N 5/0663* (2013.01); *C12N 2501/999* (2013.01); *C12N 2533/54* (2013.01); *C12N 2533/70* (2013.01); *C12N 2533/80* (2013.01); *C12N 2537/10* (2013.01)

(58) Field of Classification Search
None
See application file for complete search history.

(56) References Cited

PUBLICATIONS

Fan et al. Ectopic cartilage formation induced by mesenchymal stem cells on porous gelatin-chondroitin-hyaluronate scaffold containing microspheres loaded with TGF-beta1. Int J Artif Organs (2006), v29(6), p. 602-11.*
Johnson et al. A Stem Cell-Based Approach to Cartilage Repair. Science (2006), v336, p. 717-721 plus appended 23-page Supplemental Materials document.*
Fan et al. Gelatin Microspheres Containing TGF-3 Enhance the Chondrogenesis of Mesenchymal Stem Cells in Modified Pellet Culture. Biomacromolecules (2008), v9, p. 927-934. (Year: 2008).*

(Continued)

*Primary Examiner* — Sean C. Barron
(74) *Attorney, Agent, or Firm* — Hannah M. Tien

(57) ABSTRACT

The present invention is related to a kit comprising: (a) a mesenchymal stem cell; (b) a gelatin-hyaluronan-chondroitin tri-copolymer scaffold; (c) a kartogenin; and (d) a bioreactor. The present invention is also related to a method for promoting differentiation of a mesenchymal stem cell into cartilage tissue, comprising: (a) culturing the mesenchymal stem cell on a gelatin- hyaluronan-chondroitin tri-copolymer scaffold in the presence of a kartogenin; and (b) culturing the mesenchymal stem cell and the gelatin-hyaluronan-chondroitin tri-copolymer scaffold in a bioreactor.

4 Claims, 11 Drawing Sheets
(4 of 11 Drawing Sheet(s) Filed in Color)
Specification includes a Sequence Listing.

(56) References Cited

PUBLICATIONS

Fan et al. Porous gelatin-chondroitin-hyaluronate tri-copolymer scaffold containing microspheres loaded with TGF-beta1 induces differentiation of mesenchymal stem cells in vivo for enhancing cartilage repair. J. Biomed Mater Res (2006), v77A, p. 785-794. (Year: 2006).*

Angele et al. Characterization of esterified hyaluronan-gelatin polymer composites suitable for chondrogenic differentiation of mesenchymal stem cells. J Biomed Mater Res (2009), v91A, p. 416-427. (Year: 2009).*

Mahmoudifar N, Doran PM. Tissue engineering of human cartilage and osteochondral composites using recirculation bioreactors. Biomaterials. 2005;26(34):7012-24.

Huey DJ, Hu JC, Athanasiou KA. Unlike bone, cartilage regeneration remains elusive. Science. 2012;338 (6109):917-21.

Hunziker EB. Articular cartilage repair: basic science and clinical progress. A review of the current status and prospects. Osteoarthritis Cartilage. 2002;10(6):432-63.

Brittberg M, Lindahl A, Nilsson A, Ohlsson C, Isaksson O, Peterson L. Treatment of deep cartilage defects in the knee with autologous chondrocyte transplantation. N Engl J Med. 1994;331(14):889-95.

Mobasheri A, Csaki C, Clutterbuck AL, Rahmanzadeh M, Shakibaei M. Mesenchymal stem cells in connective tissue engineering and regenerative medicine: applications in cartilage repair and osteoarthritis therapy. Histol Histopathol. 2009;24(3):347-66.

Langer R, Vacanti JP. Tissue engineering. Science. 1993;260(5110):920-6.

Chang CH, Liu HC, Lin CC, Chou CH, Lin FH. Gelatin-chondroitin-hyaluronan tri-copolymer scaffold for cartilage tissue engineering. Biomaterials. 2003;24(26):4853-8.

Burdick JA, Vunjak-Novakovic G. Engineered microenvironments for controlled stem cell differentiation. Tissue Eng Part A. 2009;15(2):205-19.

Owen SC, Shoichet MS. Design of three-dimensional biomimetic scaffolds. J Biomed Mater Res A. 2010;94 (4):1321-31.

Chou CH, Cheng WT, Lin CC, Chang CH, Tsai CC, Lin FH. TGF-beta1 immobilized tri-co-polymer for articular cartilage tissue engineering. J Biomed Mater Res B Appl Biomater. 2006;77(2):338-48.

Beane OS, Darling EM. Isolation, characterization, and differentiation of stem cells for cartilage regeneration. Ann Biomed Eng. 2012;40(10):2079-97.

Clouet J, Vinatier C, Merceron C, Pot-vaucel M, Maugars Y, Weiss P, et al. From osteoarthritis treatments to future regenerative therapies for cartilage. Drug Discov Today. 2009;14(19-20):913-25.

Shum L, Nuckolls G. The life cycle of chondrocytes in the developing skeleton. Arthritis Res. 2002;4(2):94-106.

Quintana L, zur Nieden NI, Semino CE. Morphogenetic and regulatory mechanisms during developmental chondrogenesis: new paradigms for cartilage tissue engineering. Tissue Eng Part B Rev. 2009;15(1):29-41.

Ikeda T, Kamekura S, Mabuchi A, Kou I, Seki S, Takato T, et al. The combination of SOX5, SOX6, and SOX9 (the SOX trio) provides signals sufficient for induction of permanent cartilage. Arthritis Rheum. 2004;50(11):3561-73.

Gerber HP, Vu TH, Ryan AM, Kowalski J, Werb Z, Ferrara N. VEGF couples hypertrophic cartilage remodeling, ossification and angiogenesis during endochondral bone formation. Nat Med. 1999;5(6):623-8.

Zelzer E, Olsen BR. The genetic basis for skeletal diseases. Nature. 2003;423(6937):343-8.

Johnson K, Zhu S, Tremblay MS, Payette JN, Wang J, Bouchez LC, et al. A stem cell-based approach to cartilage repair. Science. 2012;336(6082):717-21.

* cited by examiner

Pore Diameter ( μm )

(a)

(b)

| 0 day post KGN treatment | 7 days post KGN treatment |
| 14 days post KGN treatment | 21 days post KGN treatment | a. 0 day post KGN treatment
b. 7 days post KGN treatment
c. 21 days post KGN treatment
d. 21 days post KGN treatment

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: Synthesized Actin forward primer

<400> SEQUENCE: 1
gtagccatcc aggctgtgtt                                               20

<210> SEQ ID NO 2
<211> LENGTH: 20
<212> TYPE: DNA
<213> ORGANISM: Artificial
<220> FEATURE:
<223> OTHER INFORMATION: Synthesized Actin reverse primer

<400> SEQUENCE: 2
ccctcataga tgggcagagt                                               20

<210> SEQ ID NO 3
<211> LENGTH: 20
<212> TYPE: DNA
<213> ORGANISM: Artificial
<220> FEATURE:
<223> OTHER INFORMATION: Synthesized Aggrecan forward primer

<400> SEQUENCE: 3
ggccttccct ctggatttag                                               20

<210> SEQ ID NO 4
<211> LENGTH: 17
<212> TYPE: DNA
<213> ORGANISM: Artificial
<220> FEATURE:
<223> OTHER INFORMATION: Synthesized Aggrecan reverse primer

<400> SEQUENCE: 4
ccgcactact gtccaac                                                  17

<210> SEQ ID NO 5
<211> LENGTH: 18
<212> TYPE: DNA
<213> ORGANISM: Artificial
```

```
<220> FEATURE:
<223> OTHER INFORMATION: Synthesized Col1a1 forward primer

<400> SEQUENCE: 5
tccagggctc caacgaga                                                     18

<210> SEQ ID NO 6
<211> LENGTH: 22
<212> TYPE: DNA
<213> ORGANISM: Artificial
<220> FEATURE:
<223> OTHER INFORMATION: Synthesized Col1a1 reverse primer

<400> SEQUENCE: 6
ctgtaggtga atccactgtt gc                                                22

<210> SEQ ID NO 7
<211> LENGTH: 18
<212> TYPE: DNA
<213> ORGANISM: Artificial
<220> FEATURE:
<223> OTHER INFORMATION: Synthesized Col2a1 forward primer

<400> SEQUENCE: 7
cccctgcagt acatgcgg                                                     18

<210> SEQ ID NO 8
<211> LENGTH: 22
<212> TYPE: DNA
<213> ORGANISM: Artificial
<220> FEATURE:
<223> OTHER INFORMATION: Synthesized Col2a1 reverse primer

<400> SEQUENCE: 8
ctcgacgtca tgctgtctca ag                                                22

<210> SEQ ID NO 9
<211> LENGTH: 20
<212> TYPE: DNA
<213> ORGANISM: Artificial
<220> FEATURE:
<223> OTHER INFORMATION: Synthesized Col10a1 forward primer

<400> SEQUENCE: 9
ccctattgga ccaccaggta                                                   20

<210> SEQ ID NO 10
<211> LENGTH: 20
<212> TYPE: DNA
<213> ORGANISM: Artificial
<220> FEATURE:
<223> OTHER INFORMATION: Synthesized Col10a1 reverse primer

<400> SEQUENCE: 10
tctctgtccg ctctttgtga                                                   20

<210> SEQ ID NO 11
<211> LENGTH: 20
<212> TYPE: DNA
<213> ORGANISM: Artificial
<220> FEATURE:
<223> OTHER INFORMATION: Synthesized Sox-9 forward primer

<400> SEQUENCE: 11
ctgaagggct acgactggac                                                   20
```

```
<210> SEQ ID NO 12
<211> LENGTH: 20
<212> TYPE: DNA
<213> ORGANISM: Artificial
<220> FEATURE:
<223> OTHER INFORMATION: Synthesized Sox-9 reverse primer

<400> SEQUENCE: 12
tactggtctg ccagcttcct                                               20

<210> SEQ ID NO 13
<211> LENGTH: 20
<212> TYPE: DNA
<213> ORGANISM: Artificial
<220> FEATURE:
<223> OTHER INFORMATION: Synthesized TIMP-1 forward primer

<400> SEQUENCE: 13
tttccgttcc ttaaacggcc                                               20

<210> SEQ ID NO 14
<211> LENGTH: 20
<212> TYPE: DNA
<213> ORGANISM: Artificial
<220> FEATURE:
<223> OTHER INFORMATION: Synthesized TIMP-1 reverse primer

<400> SEQUENCE: 14
gattcgacgc tgtgggaaat                                               20

<210> SEQ ID NO 15
<211> LENGTH: 20
<212> TYPE: DNA
<213> ORGANISM: Artificial
<220> FEATURE:
<223> OTHER INFORMATION: Synthesized Runx 2 forward primer

<400> SEQUENCE: 15
gccgggaatg atgagaacta                                               20

<210> SEQ ID NO 16
<211> LENGTH: 21
<212> TYPE: DNA
<213> ORGANISM: Artificial
<220> FEATURE:
<223> OTHER INFORMATION: Synthesized Runx 2 reverse primer

<400> SEQUENCE: 16
agatcgttca acctggccac t                                             21
```

KIT AND METHOD FOR PROMOTING MESENCHYMAL STEM CELL DIFFERENTIATION

The present application claims priority to Taiwan Patent Application No. 103140322 filed on 20 Nov. 2014, incorporated herein by reference in its entirety. The sequence listing text file, file name 2344-NTU-USsequencelist created Apr. 29, 2015, file size 3382 bytes, is incorporated herein by reference in its entirety.

FIELD OF THE INVENTION

The present invention is related to a kit and method for promoting differentiation of a mesenchymal stem cell into cartilage tissue.

BACKGROUND OF THE INVENTION

Normal cartilage surface is a smooth surface without fracture or defects. Because the cartilage is a tissue without vascular, nervous and lymphatic system, the mature cartilage cells have limited repair capability to the damage caused by disease or injury (Mahmoudifar N, Doran P M. Tissue engineering of human cartilage and osteochondral composites using recirculation bioreactors. Biomaterials. 2005;26(34):7012-24). In addition, as lacking nervous tissue, the damage at early stage is not noticed. Because of lacking blood vessels, nutrients and progenitor cells in the blood cannot reach to the damaged area of the cartilage; self repair capability of the cartilage is limited.

The cell density of the tissue is very low; therefore, the damaged part of the cartilage cannot be repaired by the cell in time. The repair capability of the cartilage and that of bone are different, the latter has wider blood vessel distribution, providing sufficient blood nutrients and stem cells, and therefore a considerable degree of damage can be repaired (Huey D J, Hu J C, Athanasiou K A. Unlike bone, cartilage regeneration remains elusive. Science. 2012;338 (6109):917-21).

Cartilage relies on synovial fluid infiltration to meet their nutrient needs. The lack of cell and related repair factors makes that even a small area of cartilage damage cannot be repaired successfully (K. A. Athanasiou EMD, J. C. Hu, Synth. Lect. Tissue Eng. 1, 1 2009). Articular cartilage damages are mostly caused by the joint trauma, abnormal joint loading or degenerative joint disease.

In the most severe situation of joint damage, patients cannot endure the pain to seriously affects their daily lives; so that osteotomy and artificial joint replacement are needed. Because cartilage is an extremely slow self repair tissue, a small area of joint damage in the condition of losing the normal physiological function of cartilage require to take other treatments in order to achieve relieving discomfort or cartilage repair purposes. For example, the treatment methods are injection treatment, drilling, autologous osteochondral transplantation and autologous chondrocyte transplantation.

Autologous osteochondral transplantation is a one-time surgery. The cartilage region of the unstressed joint area, together with subchondral bone is simultaneously removed and transplanted to the defect area. The disadvantage of the surgery is that the donation area lacks cartilage, and it is difficult to perform when the damaged area is larger than 4 $cm^2$ (Hunziker E B. Articular cartilage repair: basic science and clinical progress. A review of the current status and prospects. Osteoarthritis Cartilage. 2002;10(6):432-63). Furthermore, the transplanted cartilage may not be perfectly integrated into the defect area.

The autologous chondrocyte transplantation requires two surgeries. In the first surgery, chondrocytes isolated from cartilage tissue removed from patient's unstressed healthy cartilage are amplified in vitro to operate the second surgery (Brittberg M, Lindahl A, Nilsson A, Ohlsson C, Isaksson O, Peterson L. Treatment of deep cartilage defects in the knee with autologous chondrocyte transplantation. N Engl J Med. 1994;331(14):889-95) in which the chondrocytes are collected and injected into the defect area, and is covered by the periosteum. The disadvantages of the transplantation are its complex process, and in the in vitro amplification process, the cartilage may lose its original morphology. Furthermore, the cellular fluid may also be exposed during the treatment of the outer periosteal suture (Mobasheri A, Csaki C, Clutterbuck A L, Rahmanzadeh M, Shakibaei M. Mesenchymal stem cells in connective tissue engineering and regenerative medicine: applications in cartilage repair and osteoarthritis therapy. Histol Histopathol. 2009;24(3):347-66).

Given from above, there lacks an ideal treatment for joint injuries. The autologous chondrocyte transplantation is currently popular therapy. However, healthy cartilage has to be removed from the patient's body as a result of lacking cartilage in donation area. Therefore the inventor uses tissue engineering methods for culturing tissues having cartilage characteristics from patient's autologous mesenchymal stem cells to facilitate cartilage transplantation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
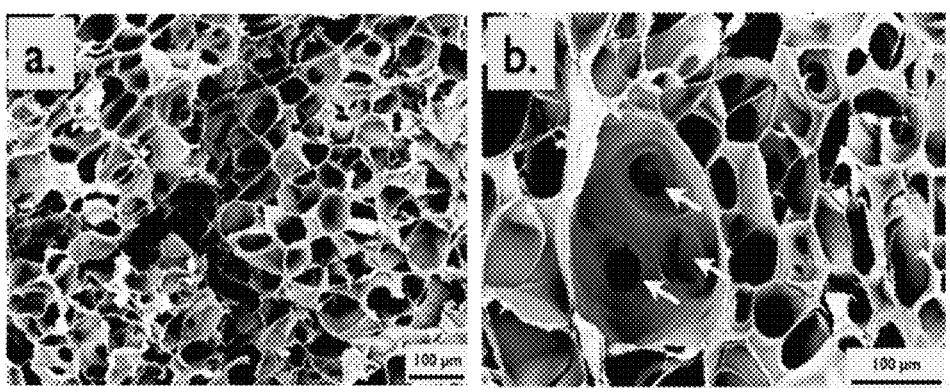
FIG. 1 shows the scanning electron microscopic image of the gelatin-hyaluronan-chondroitin tri-copolymer scaffold that (a) the pores of the synthetic sponge scaffold distribute in uniform stage; and (b) the pores are interconnected. The pore size under the electron microscopy observation is smaller than that in the cell culture. It is because after the scaffold absorbs the medium and swells, the pore size expands.

The present invention provides a kit comprising: (a) a mesenchymal stem cell; (b) a gelatin-hyaluronan-chondroitin tri-copolymer scaffold; (c) a kartogenin; and (d) a bioreactor. The present invention also provides a method for promoting differentiation of a mesenchymal stem cell into cartilage tissue, comprising: (a) culturing the mesenchymal stem cell on a gelatin-hyaluronan-chondroitin tri-copolymer scaffold in the presence of a kartogenin; and (b) culturing the mesenchymal stem cell and the gelatin-hyaluronan-chondroitin tri-copolymer scaffold in a bioreactor.

DETAIL DESCRIPTION OF THE INVENTION

Unless otherwise specified, "a" or "an" means "one or more".

Tissue engineering is defined as using a substitute having biological functionality to replace, maintain or strengthen the function lost in defects, diseases or accidents (Langer R, Vacanti J P. Tissue engineering. Science. 1993;260(5110): 920-6).

Relative to other tissues, articular cartilage is simple in its structure, so it was forecast to be the first successful tissue engineering products, but this has been overturned. It is needed to consider the types of cells and scaffolds being used in successful cartilage tissue engineering, and the products need to have the same mechanical properties.

In order to provide the growth environment suitable for the particular cells using in the defect repair, the scaffold should be able to maintain the function of the cells and has good biocompatibility and biodegradability. The degraded products can be metabolized by the organism with no toxic, and are replaced by the new generated extracellular matrix. Natural polymeric materials are the options meet this requirement; especially the materials similar to natural extracellular matrix component, which can help cells attaching and also help maintaining the chondrocyte morphology (Chang C H, Liu H C, Lin C C, Chou CH, Lin F H. Gelatin-chondroitin-hyaluronan tri-copolymer scaffold for cartilage tissue engineering. Biomaterials. 2003;24(26): 4853-8).

In the traditional 2-dimensional cell culture, cell-cell only has a very small part of contact area, half of the cell area contacts with the cell culture plate, while the other half contacts with the medium (Burdick J A, Vunjak-Novakovic G. Engineered microenvironments for controlled stem cell differentiation. Tissue Eng Part A. 2009;15(2):205-19). The three-dimensional culture environment provides additional niche, which is: having the function for better biochemical signals in guiding cell, providing the function for cell migration within the scaffold, increasing the cell density and the signal transduced between cells, providing cell adhesion molecules, and inducing cell differentiation (Owen S C, Shoichet M S. Design of three-dimensional biomimetic scaffolds. J Biomed Mater Res A. 2010;94(4):1321-31). The sponge three-dimensional scaffold, if the pore size is greater than 50 µm, promotes cell migration, thereby promoting cell condensation in cartilage differentiation path. In addition, the interlinked porous structure makes the cell seeding and nutrients diffusing more evenly.

Traditionally, many cartilage tissue engineerings use the synthetic polymers such as poly glycolic acid (PGA), poly lactic acid (PLA) or poly lactic-co-glycolic acid (PLGA) to fabricate the scaffolds. However, these materials have disadvantages such as its hydrophobicity or lack of biological activity. Past studies showed that gelatin-hyaluronan-chondroitin copolymer support the maintenance of cell morphology in the chondrocyte culturing process (Chou C H, Cheng W T, Lin C C, Chang C H, Tsai C C, Lin F H. TGF-beta1 immobilized tri-co-polymer for articular cartilage tissue engineering. J Biomed Mater Res B Appl Biomater. 2006; 77(2):338-48).

Mesenchymal stem cell belongs to pluripotent stem cell. It was found in the 1960s that it can differentiate into cartilage, bone, fat and other tissues. The stem cell exists in vivo in a plurality of portions such as bone marrow, umbilical cord, fat, placenta, etc (Beane O S, Darling E M. Isolation, characterization, and differentiation of stem cells for cartilage regeneration. Ann Biomed Eng. 2012;40(10): 2079-97). Because mesenchymal stem cell has adhesion property that gives the advantage of easy separation. Further, during 2-dimensional cell culture and in the case of increasing number, the cell can still maintain its pluripotency (Clouet J, Vinatier C, Merceron C, Pot-vaucel M, Maugars Y, Weiss P, et al. From osteoarthritis treatments to future regenerative therapies for cartilage. Drug Discov Today. 2009;14(19-20):913-25). In addition, because it is at lower level of stem cells, compared to embryonic stem cells, the differentiation path can be more regulated, and preventing tumor producing. All in all, the adult mesenchymal stem cell is a potential cell source for cartilage engineering.

Because of the improvement of the technology in isolating stem cells from patients, cartilage produced by self mesenchymal stem cells can avoid allograft rejection. Even in allograft, mesenchymal stem cells have also been shown having immunosuppressive activity in recent studies, especially for T cell immunosuppression.

In embryogenesis, mesenchymal stem cells differentiate into chondroblast after proliferation and further proliferate to chondrocyte. Cartilage helps to support structures in the development stage of endochondral ossification (EO) (Shum L, Nuckolls G. The life cycle of chondrocytes in the developing skeleton. Arthritis Res. 2002;4(2):94-106). Chondrogenesis comprises the stages of condensation, chondrocyte hypertrophy and endochondral ossification.

The first stage is the proliferation and condensation of the stem cells. At this stage, the number of the stem cell is increased, and the distance between one another is condensed. This increases the signal transduction between cells, and the interaction between cells and the extracellular matrix (Quintana L, zur Nieden N I, Semino C E. Morphogenetic and regulatory mechanisms during developmental chondrogenesis: new paradigms for cartilage tissue engineering. Tissue Eng Part B Rev. 2009;15(1):29-41). Many adhesion proteins are expressed at this stage, for example N-cadherin, focal adhesion kinase and neural cell addhesion molecule (N-CAM) and so on. In the process of stem cells condensation, the gene Sox-9 is the representative transcription factor which assists in regulating other cartilage related genes comprising Sox5 and Sox6 (together called Sox trio), which can jointly attach to and regulate chondroproteoglycan and type II collagen gene fragments (Ikeda T, Kamekura S, Mabuchi A, Kou I, Seki S, Takato T, et al. The combination of SOX5, SOX6, and SOX9 (the SOX trio) provides signals sufficient for induction of permanent cartilage. Arthritis Rheum. 2004;50(11):3561-73). The secretion of extracellular matrix is also promoted by regulating proteins such as cAMP response element binding protein (CREB), p300, PGC-1α, T-cell factor and Sox family protein.

In the chondrocyte hypertrophy and endochondral ossification stage, cartilage tissue has been formed. In the embryonic development, cartilage has two fates, the first one is to maintain cartilage morphology forever, and the other one called endochondral ossification. In this case, chondrocytes stop proliferating, leave the cell cycle and hypertrophy starts. This is the first indication of endochondral ossification. After that, the extracellular matrix begins to degrade and the secreted constituent is also changed. Type II collagen and type IX collagen are reduced, on the contrary, the expression of type X collagen and alkaline phosphatase are increased. Before entering apoptosis, hypertrophic chondrocytes begin progressing mineralization and accumulating vascular endothelial growth factor. The following vasculogenesis and angiogenesis let blood vessels grow into the extracellular matrix (Gerber H P, Vu T H, Ryan A M, Kowalski J, Werb Z, Ferrara N. VEGF couples hypertrophic cartilage remodeling, ossification and angiogenesis during endochondral bone formation. Nat Med. 1999;5(6):623-8). It brings osteoblasts, chondroclasts etc. into the space of the extracellular matrix, and the bone tissue starts forming.

The regulations of this stage comprise, for example gene Runt-related transcription factor 2 (Runx 2) promotes chondrocytes going to hypertrophy, and Sox-9 suppress the situation (Zelzer E, Olsen B R. The genetic basis for skeletal diseases. Nature. 2003;423(6937):343-8). To understand and utilize this part of regulations are critical in cartilage tissue engineering, it promotes producing stable cartilage products.

In the past cartilage tissue engineering, the inducing signals for cell differentiation were mostly protein growth factors. In 2012, Johnson and his colleagues examined 20,000 heterocyclic compounds by the sequences and screened the small molecules which can induce cell differentiation from them. In the 20,000 compounds, one compound—kartogenin (KGN) can promote human mesenchymal stem cells forming cartilage nodules and can be used in cartilage tissue regeneration (Johnson K, Zhu S, Tremblay M S, Payette J N, Wang J, Bouchez L C, et al. A stem cell-based approach to cartilage repair. Science. 2012;336 (6082):717-21). This implies for another advantage that compared to the growth factor the price of the compound is affordable for most patients.

Bioreactor refers to any suitable environment or engineering devices providing biochemical reactions. It usually refers to the use of enzymes (driven by one or a group of enzymes) or organisms (e.g., microorganisms) that makes the apparatus having the biomimetic functions which the biochemical reactions can be performed outside the cell. In the mimetic process, not only aerobic reaction but also anaerobic reaction can be performed. These systems are quite important devices in the applications of liquor, tissue engineering, biochemical engineering, pharmaceutical production and degradation of organic pollutants . . . and so on.

Therefore, the present invention provides a kit comprising: (a) a mesenchymal stem cell; (b) a gelatin-hyaluronan-chondroitin tri-copolymer scaffold; (c) a kartogenin; and (d) a bioreactor.

Based on the kit of the present invention, in a preferred embodiment, it promotes the mesenchymal stem cell to differentiate into cartilage tissue after 3-21 days of culture. In a more preferred embodiment, it promotes the mesenchymal stem cell to differentiate into cartilage tissue after 7-21 days of culture. In another more preferred embodiment, it promotes the mesenchymal stem cell to differentiate into cartilage tissue after 14-21 days of culture and the cartilage tissue comprises lacunae structure.

Based on the kit of the present invention, in a preferred embodiment, the concentration of the kartogenin is 0.03-2 µM. In a more preferred embodiment, the concentration of the kartogenin is 0.05-1.5 µM. In another more preferred embodiment, the concentration of the kartogenin is 0.1-1 µM. In another embodiment, the outer pore of the gelatin-hyaluronan-chondroitin tri-copolymer scaffold is smaller than the inner pore of the scaffold.

The present invention further provides a method for promoting differentiation of a mesenchymal stem cell into cartilage tissue, comprising: (a) culturing the mesenchymal stem cell on a gelatin-hyaluronan-chondroitin tri-copolymer scaffold in the presence of a kartogenin; and (b) culturing the mesenchymal stem cell and the gelatin-hyaluronan-chondroitin tri-copolymer scaffold in a bioreactor.

Based on the method of the present invention, in a preferred embodiment, it promotes the mesenchymal stem cell differentiating into cartilage tissue after 3-21 days of culture. In a more preferred embodiment, it promotes the mesenchymal stem cell differentiating into cartilage tissue after 7-21 days of culture. In another more preferred embodiment, it promotes the mesenchymal stem cell differentiating into cartilage tissue after 14-21 days of culture and the cartilage tissue comprises lacunae structure.

Based on the method of the present invention, in a preferred embodiment, the concentration of the kartogenin is 0.03-2 µM. In a more preferred embodiment, the concentration of the kartogenin is 0.05-1.5 µM. In another more preferred embodiment, the concentration of the kartogenin is 0.1-1 µM. In another embodiment, the outer pore of the gelatin-hyaluronan-chondroitin tri-copolymer scaffold is smaller than the inner pore of the scaffold. The bioreactor of the present invention comprises but is not limited to the Bioreactor system disclosed in U.S.20060148078.

EXAMPLES

The examples below are non-limiting and are merely representative of various aspects and features of the present invention.

Example 1

The Analysis of Gelatin-Hyaluronan-Chondroitin Tri-Copolymer Material

The material of the tri-copolymer Gelatin, hyaluronic acid and chondroitin-6-sulfate were crosslinked by 1-Ethyl-3-(3-dimethylaminopropyl) carbodiimide (EDC) and N-Hydroxysuccinimide (NHS). 0.5 g of gelatin, 5 mg of hyaluronic acid and 0.1 g of chondroitin-6-sulfate were in turns dissolved in 8 mL of ddH$_2$O at 40° C. . After 30 minutes of stirring, the solution was poured into the 48 well culture plate as template and 200 µL of EDC/NHS crosslinking agent was added into each well. The reacting concentration of EDC was 10 mM and NHS was 4 mM. NHS can stabilize the easily hydrolysed iso-acylurea produced by the crosslinking process and makes better reacting efficiency. The crosslinking reaction was carried out at room temperature for 30 minutes and was moved to 4° C. for 1 hour. Then the solution was moved to −20° C. After freezing, it was moved to freeze dryer and freeze-dried for 72 hours. During the freeze-drying process, the material was converted to sponge structure. The material was then immersed in 10 mL of EDC/NHS crosslinking solution for 48 hours. Urea was removed by ddH$_2$O. The clean material was moved into 75% alcohol for sterilization, washed by sterile water and freeze-dried for cell seeding. The component of the tri-copolymer scaffold was as follows:

| | |
|---|---|
| gelatin | 5% wt |
| chondroitin-6-sulfate | 1% wt |
| hyaluronic acid | 0.05% wt |
| 1-Ethyl-3-(3-dimethylaminopropyl) carbodiimide | 10 mM |
| N-Hydroxysuccinimide | 4 mM |

Electron microscope is the microscope using electron as illuminating light source. A scanning electron microscope mainly comprises two parts, body and the imaging system. The water was removed from the tri-copolymer scaffold by series alcohol dehydration method (25%, 50%, 75%, 90%, 100%). To identify the micro-structure, the scaffold was completely dehydrated, immersed in liquid nitrogen, and sectioned by the knife The scaffold was then gold-plated and the scanning electron microscope sample preparation was completed.

The scanning electron microscopic image of the gelatin-hyaluronan-chondroitin tri-copolymer scaffold was shown in FIG. 1 (a) which was a sponge material with high porosity and the pores distributed homogeneously. The pore structures were interconnected (FIG. 1 (b)) for helping the nutrition permeation (Burdick J A, Vunjak-Novakovic G. Engineered microenvironments for controlled stem cell differentiation. Tissue Eng Part A. 2009;15(2):205-19). In fact, the pore diameter shown in the scanning electron microscopic image was getting bigger after absorbed the medium and swelled.

Figure 2:
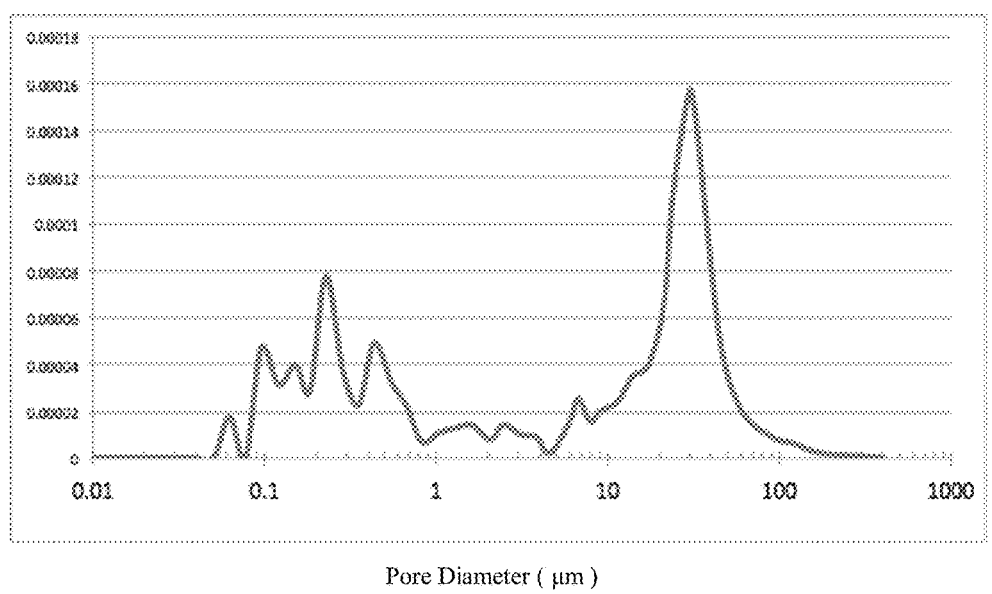
FIG. 2 shows the pore diameter distribution of the gelatin-hyaluronan-chondroitin tri-copolymer scaffold. Through converting the applied pressure and the corresponding pore diameter, differentiating the mercury volume infiltrated to tri-copolymer with respect to the corresponding pore diameter, the pore diameter distribution can be illustrated.
Figure 3:
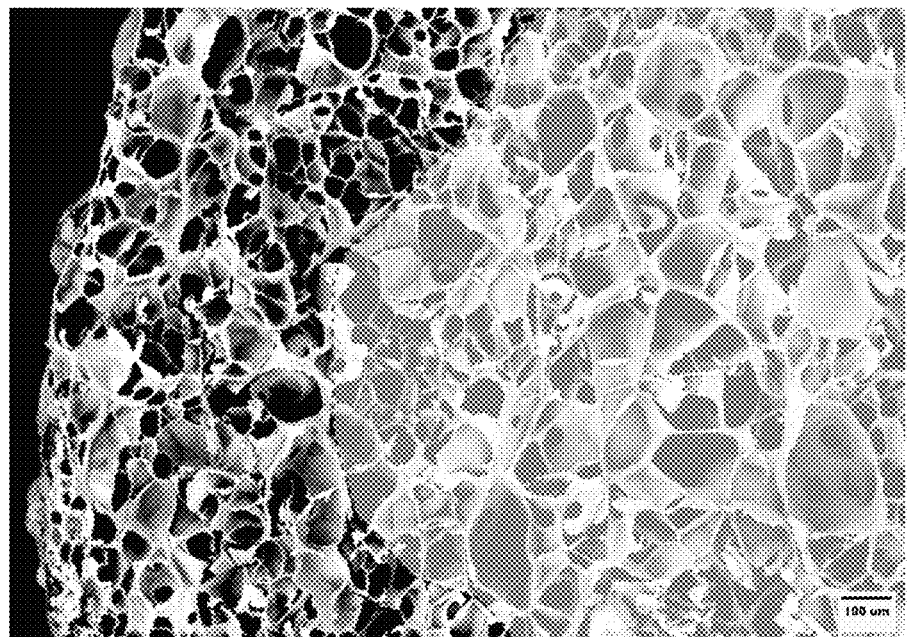
FIG. 3 shows the distribution of the inner and outer layer of the pore of the scaffold. The freeze-dried outer material is composed of the part of the smaller pore. The smaller pore structure helps to keep the cells inside the material after seeding the cells into the sponge material.

The porosity, pore size and the pore distribution were measured by mercury intrusion porosimeter. The bulk density of the gelatin-hyaluronan-chondroitin tri-copolymer scaffold was 0.153 g/cm$^3$ and the porosity was 91%. The high permeability also helped the cell migration and the infiltration of the medium. Through converting the impressed pressure and the corresponding pore diameter, differentiated the mercury volume infiltrated to tri-copolymer with respect to the corresponding pore diameter, the pore diameter distribution was described (FIG. 2). In fact, the outer material under freeze dried is composed of the part of the smaller pore (FIG. 3). The smaller pore structure helped to keep the cells inside the material after seeding the cells into the sponge material.

The crosslinking degree was analyzed by 2,4,6-trinitrobenzenesulfonic acid (TNBS) method. The principle was that in gelatin, abundant lysine and hydroxylysine were labeled on ∈-amino by 2,4,6-trinitrobenzenesulfonic acid and could be detected by UV spectrophotometer.

Figure 4:
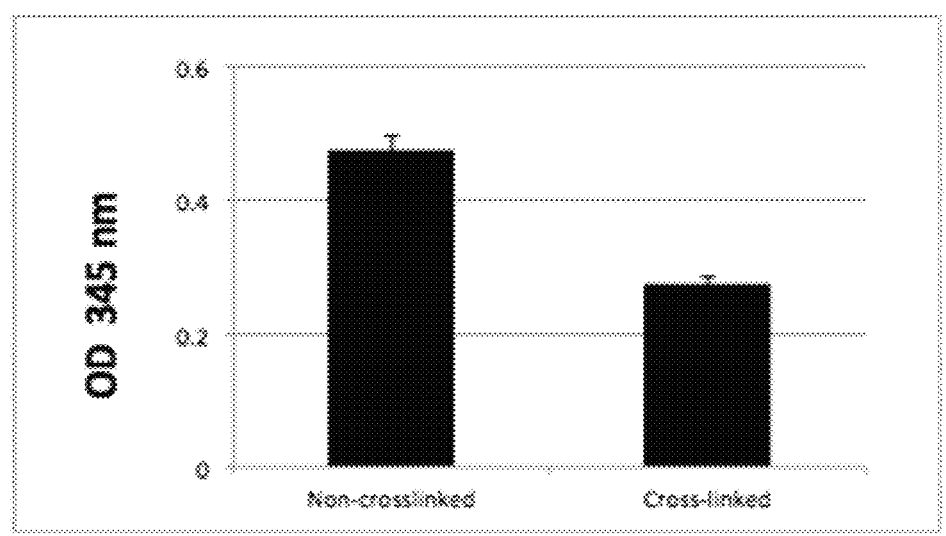
FIG. 4 shows the result of the crosslinking degree of 2,4,6-trinitrobenzenesulfonic acid (TNBS). Using the TNBS method, the crosslinking degree is estimated as 42.2% by the $OD_{345}$ value.

The crosslinking degree was analyzed by 2,4,6-trinitrobenzenesulfonic acid (TNBS) method. The crosslinking situation of the tri-copolymer was inverse estimated by the OD$_{345}$ value (FIG. 4). The OD$_{345}$ value of the crosslinked scaffold was 0.275±0.009 and the $OD_{345}$ value of the uncrosslinked was 0.476±0.021, the crosslinking degree was estimated as 42.2%. In the present invention, dynamic culture environment was used for culturing, so the crosslinking degree needed to achieve certain level. For the following 21 days of bioreactor culture, this crosslinking degree (42.2%) sufficiently supported the scaffold material maintaining the morphology.

Example 2

The Establishment of Stem Cell Colonies and the Differentiation Effect Test of the Kartogenin The Isolation and Culture of the Mesenchymal Stem Cell
1. The cell source was taken from the four limbs of two-week old Wistar rats. Rats were sacrificed and immersed in 75% alcohol. The operation process for taking four limbs was under half sterile environment.
2. During the cellular collecting processes, sterilized equipments were used in the whole processes. Both tibia and femur of the lower limb were taken. The tip of the scissor was used to separate the bone and the muscle. The knee joints and the hip joints were taken down along the bones; the part near the ankle was difficult to remove completely, so a direct cut was made close to the ankle joints. Only the humerus in upper limb had enough amounts of cells, so just took humerus and the scapula was processed as ankle joints in having a direct cut. Finally the limbs were soaked and washed in phosphate buffer solution (PBS) with 10% antibiotics (penicillin 10,000/ml, streptomycin 10 mg/ml, amphotericin-B 0.025 mg/ml).
3. The muscle on the limbs was clearly removed under solution, the protruding parts of the two ends were cut out and soaked into new PBS (containing 1% antibiotics). Cells were washed out by syringe filled with PBS.
4. PBS containing cells was placed in centrifuge tubes and centrifugated at 2000 rpm for 5 minutes. The red blood cells were suspended cells which adhered to and flowed with the mesenchymal stem cell. The supernatant was carefully removed.
5. Hank's Balanced Salt Solution (HBSS) was added into the centrifugated cells. After mixing up, 5 mL of HBSS mixed with cells was added into 5 mL of Ficoll separating solution and centrifugated at 18-20° C. at the speed 300 g for 40 minutes.
6. After centrifugation, the supernatant was sucked out; large amount of PBS was added to dilute the Ficoll separating solution and washed for 2-3 times.
7. Medium was added into the centrifugated cells and mixed up for culturing. Dulbecco's Modified Eagle Medium (DMEM) with 10% fetal bovine serum (FBS) was used for the stem cell medium in this example.
8. After the cells attached, the medium was changed every 2-3 days. When the cells was fully confluent, subcultured as the proportion of one to three or one to four.

The mesenchymal stem cells obtained from bone marrow expressed CD29, CD44, CD90 but not CD45. In the present invention, these cell markers were used to confirm that the cells used were mesenchymal stem cell populations. The flow cytometry of the present invention equipped with one 488 nm excitation laser light, the analyzing steps were as follows:
1. The fully confluent cultured fourth generation cells were collected and the cell number was confirmed by cell counting.
2. Cells were washed by PBS and a million of cells were dispensed to each flow cytometry tube.
3. Preparation of the antibody binding solution (staining buffer): 2% of FBS in PBS.
4. After centrifugation, the supernatant was discarded; the appropriate concentration of the antibody (diluted with the antibody binding solution) was added, reacted at 4° C. in the dark for 30 minutes and centrifugated at 1600 rpm for 5 minutes.
5. The supernatant was sucked out; the cells were dispersed evenly and assayed with the flow cytometry.

Figure 5:
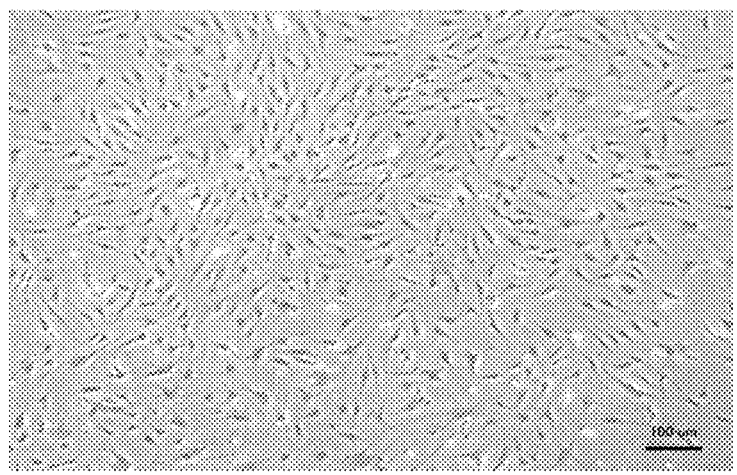
FIG. 5 shows the qualitative analysis of the mesenchymal stem cell: (a) the cell morphology of the third generation mesenchymal stem cell; (b) the labeling distribution of the stem cell population. The population expressing CD44, CD90 and CD29 is more than 98% of the total. The lower right shows the binding situation of the antibody isotype. The four quadrants are demarcated by the antibody isotype signal.
Figure 5:
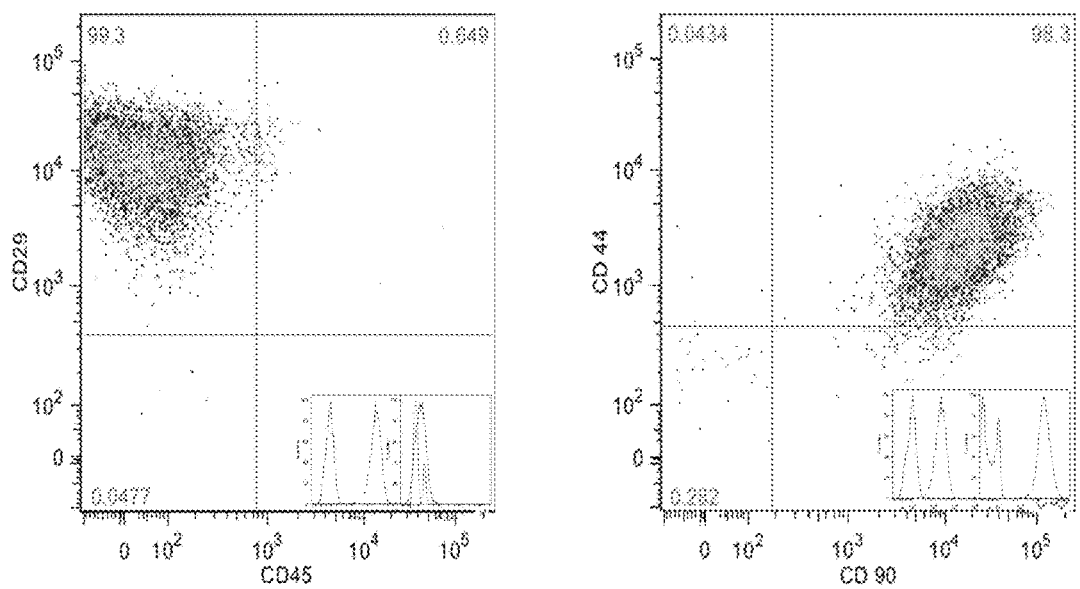

The mesenchymal stem cells were isolated by 4-week old Wistar rats, cultured to the third generation and characterized for the cell marker by the flow cytometry. FIG. 5(a) showed the cell morphology of the third generation mesenchymal stem cell which was spindle-shaped. FIG. 5(b) showed the qualitative results of the stem cell population. The population was $CD29^+$, $CD44^+$, $CD90^+$, $CD45^-$ and the population expressing CD44, CD90 and CD29 was greater than 98% of the total. This showed that the cells used in the example had stem cell properties.

Figure 6:
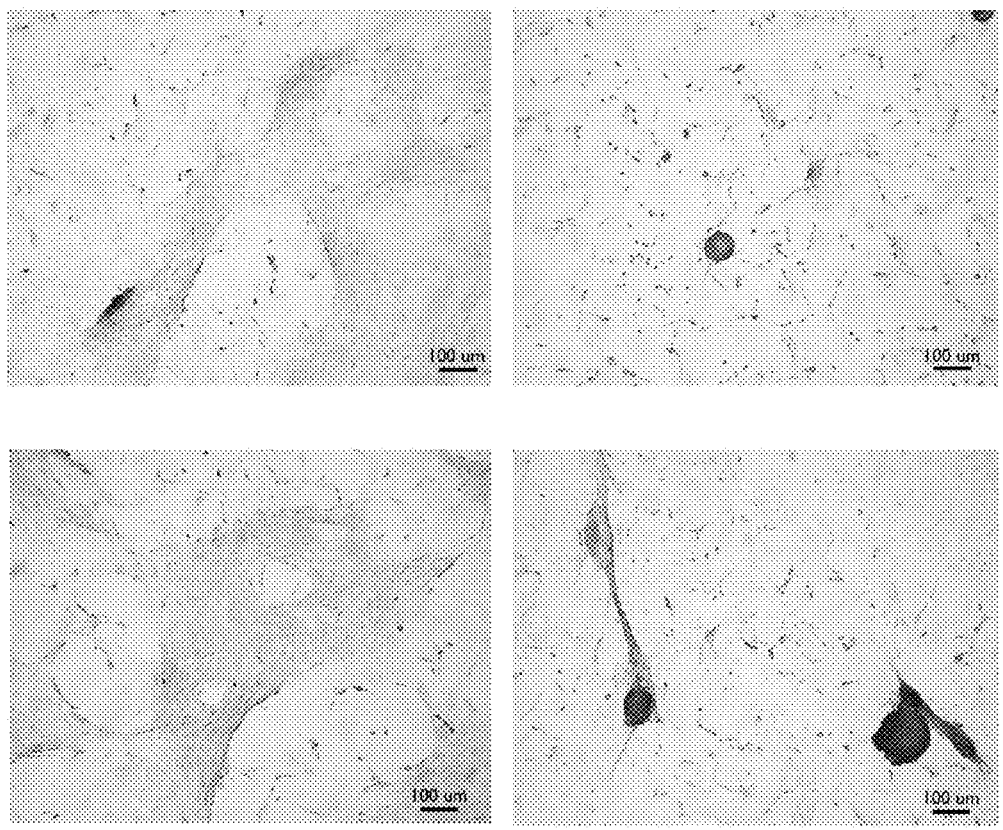
FIG. 6 shows the condensation situation of the mesenchymal stem cell culturing on the 2-dimensional plate at 0.1 μM kartogenin for (a) 3 days or (b) 7 days and at 1.0 μM kartogenin for (c) 3 days or (d) 7 days respectively. Blue represents the secretion of glycosaminoglycans, and red is the cytoplasm staining

Before combining the gelatin-hyaluronan-chondroitin tri-copolymer and the mesenchymal stem cell, the differentiation effects were first confirmed in the 2-dimensional plate culturing environment. Through Alcian Blue stain, whether 0.1 µM ($EC_{50}$ of hMSC) and 1.0 µm of kartogenin helped the mesenchymal stem cell early condensation and the secretion of glycosaminoglycans (GAGs) were examined. As shown in FIG. 6, compared to the control group without kartogenin administration, in groups of 0.1 µm and 1.0 µm, 3 days after administering the drug, the cells appeared the shrinking phenomenon. When it reached 7 days of post treatment, the cell mass expressing glycosaminoglycans appeared. These results showed that both 0.1 µM and 1.0 µM of kartogenin promoted the condensation phenomenon in the early chondrocyte differentiation.

The gene expression of the mesenchymal stem cell was examined by Real-time PCR. The results were used for determining the medium formulation in the following scaffold culture and bioreactor culture. The primers used in the present invention were shown as the following table:

| Gene | | Primer | SEQ ID NO |
|------|---|--------|-----------|
| Actin | Forward | GTAGCCATCCAGGCTGTGTT | SEQ ID NO: 1 |
| | Reverse | CCCTCATAGATGGGCAGAGT | SEQ ID NO: 2 |
| Aggrecan | Forward | GGCCTTCCCTCTGGATTTAG | SEQ ID NO: 3 |
| | Reverse | CCGCACTACTGTCCAAC | SEQ ID NO: 4 |
| Col1a1 | Forward | TCCAGGGCTCCAACGAGA | SEQ ID NO: 5 |
| | Reverse | CTGTAGGTGAATCCACTGTTGC | SEQ ID NO: 6 |
| Col2a1 | Forward | CCCCTGCAGTACATGCGG | SEQ ID NO: 7 |
| | Reverse | CTCGACGTCATGCTGTCTCAAG | SEQ ID NO: 8 |

-continued

| Gene | | Primer | SEQ ID NO |
|---|---|---|---|
| Col10a1 | Forward | CCCTATTGGACCACCAGGTA | SEQ ID NO: 9 |
| | Reverse | TCTCTGTCCGCTCTTTGTGA | SEQ ID NO: 10 |
| Sox-9 | Forward | CTGAAGGGCTACGACTGGAC | SEQ ID NO: 11 |
| | Reverse | TACTGGTCTGCCAGCTTCCT | SEQ ID NO: 12 |
| TIMP-1 | Forward | TTTCCGTTCCTTAAACGGCC | SEQ ID NO: 13 |
| | Reverse | GATTCGACGCTGTGGGAAAT | SEQ ID NO: 14 |
| Runx 2 | Forward | GCCGGGAATGATGAGAACTA | SEQ ID NO: 15 |
| | Reverse | AGATCGTTCAACCTGGCCACT | SEQ ID NO: 16 |

Figure 7:
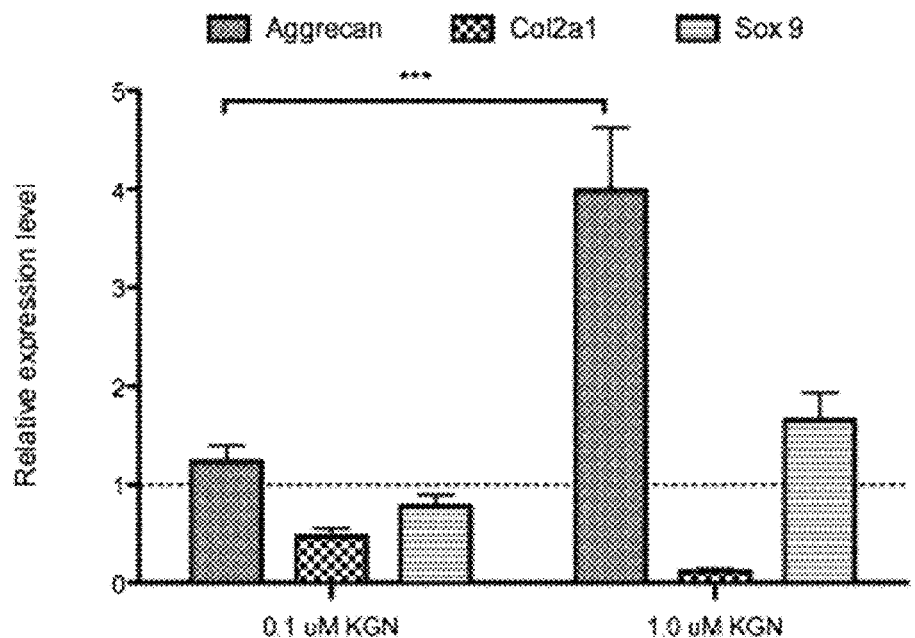
FIG. 7 shows the gene examination of the mesenchymal stem cell culturing on the plate for 7 days. Adding 1.0 μM kartogenin, the cartilage-specific gene Aggrecan is higher (3.99±0.63-fold) than the addition of 0.1 μM and has significant difference ($p<0.001$). Furthermore, Sox-9 gene relative to the control group, is also up-regulated (1.66±0.27-fold); ($n=3*p<0.05***p<0.001$).

The cells cultured in DMEM with 10% FBS were used as the control group. This showed that between the concentrations of 0.1 μM and 1.0 μM kartogenin, which one had higher correlation with the chondrogenic differentiation specific gene. FIG. 7 was the group cultured on 2-dimensional plane for 7 days, and showed that cartilage specific gene Aggrecan was higher in 1.0 μM group than in 0.1 μM group (3.99±0.63-fold) and had significant differences (p<0.001). Furthermore Sox-9 gene relative to the control group was also up-regulated (1.66±0.27-fold).

Figure 8:
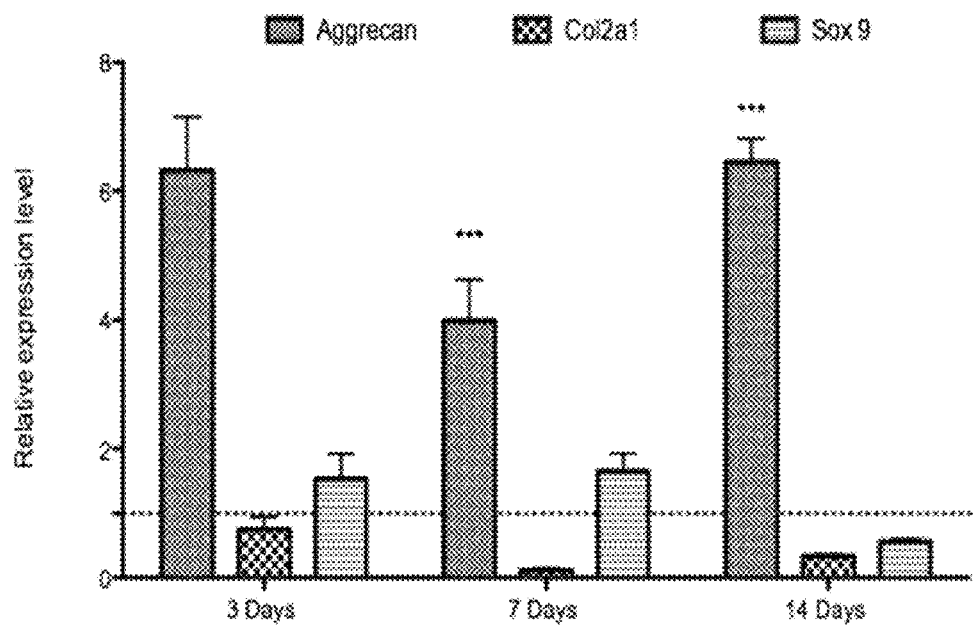
FIG. 8 shows the gene examination of the mesenchymal stem cell culturing at 1.0 μM kartogenin on the 2-dimensional plate for 14 days. Under 2-dimensional culturing at 1.0 μM kartogenin for 14 days, the gene Aggrecan has significant difference ($p<0.001$) with 0.1 μM. Chondrocyte differentiation regulating gene Sox-9 is up-regulated in the 3 and the 7 days of culture. The expression of tissue inhibitors of metallproteinases (TIMPs) at day 14 is higher in 1.0 μM group ($n=3*p<0.05***p<0.001$).

Compared to the untreated group, the expression of Aggrecan gene was 6.44±0.35 fold higher in the 1.0 μM group of 14 days 2-dimensional plate culture (FIG. 8) and had significant differences with the 0.1 μm group (p<0.001). Chondrocyte differentiation regulating gene Sox-9 was up-regulated at day 3 and day 7 and down-regulated at day 14 (0.56±0.04 fold).

However, the expression of tissue inhibitors of metallproteinases (TIMPs) at day 14 was examined. The 1.0 μM group compared to the control group, increased to 1.63±0.249 fold and was higher than 0.91±0.04 fold of the 0.1 μM group. Taken the above, for the 3-dimensional scaffold culture, 1.0 μM of kartogenin was selected for the optimal concentration for the further examples.

Example 3

The Differentiation of the Stem Cells in the Gelatin-Hyaluronan-Chondroitin Tri-Copolymer The mesenchymal stem cells used in the present invention were in the third generation of subculture to ensure the maintenance of the cell morphology. The proliferated stem cells were dissociated by trpsin, collected and condensed to $10^7$ cells/mL. 50 μL of the cell solution was seeded on each dry scaffold. The cells were divided into static culture group and bioreactor culture group. The former changed the medium every 2 to 3 days and in the latter, after cells seeding into the scaffold and culturing for one day, it was moved into the bioreactor.

Figure 9:
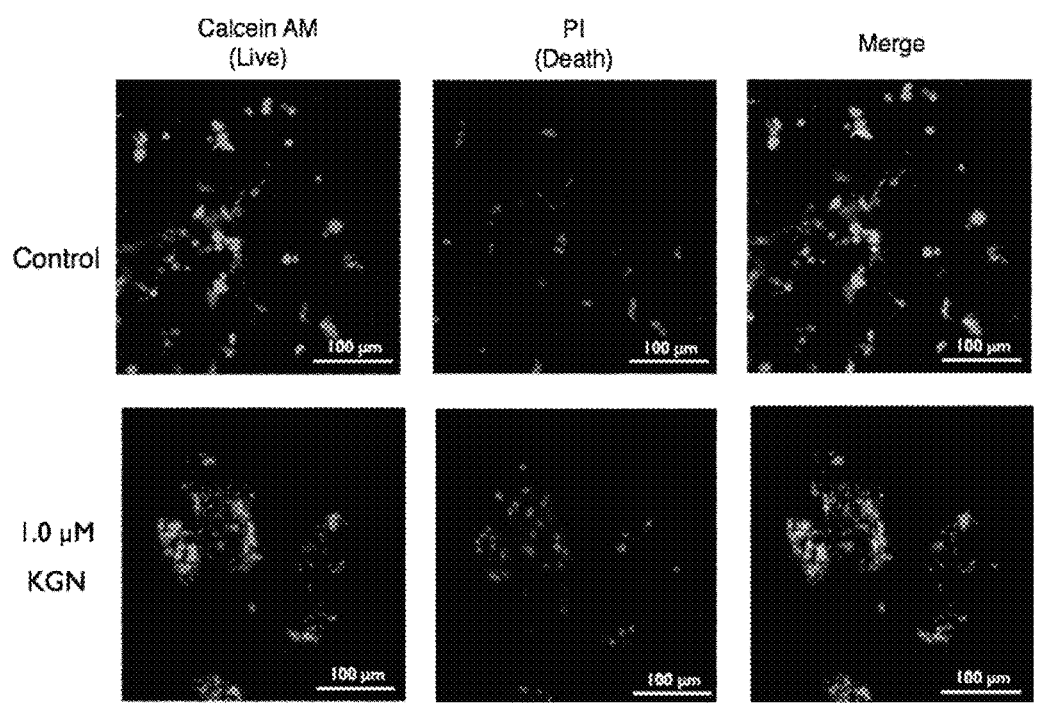
FIG. 9 shows the condensation examination of the mesenchymal stem cell culturing inside the scaffold for 7 days. Through the survival staining, the cell condensation is examined. Green is for Calcein AM which represents the living cells. Red is for propidium iodide (PI) which represents the dead cells; scale bar=100 μm.

FIG. 9 showed the cell survival staining of the control group and 1.0 μM kartogenin group for 7 days of culture. After the combination of the gelatin-hyaluronan-chondroitin tri-copolymer with the mesenchymal stem cell, the differentiating effects under the 3-dimensional culture were confirmed. Through the live and death staining, the cell condensation during early differentiation stage was examined at the presence of 1.0 kartogenin. As shown in FIG. 9, compared to the homogeneous distribution of cells in control group, cell condensation was occurred in the group with the presence of kartogenin and the proportion of cell death was also higher. Apoptosis was the process during chondrogenic differentiation of stem cell.

Figure 10:
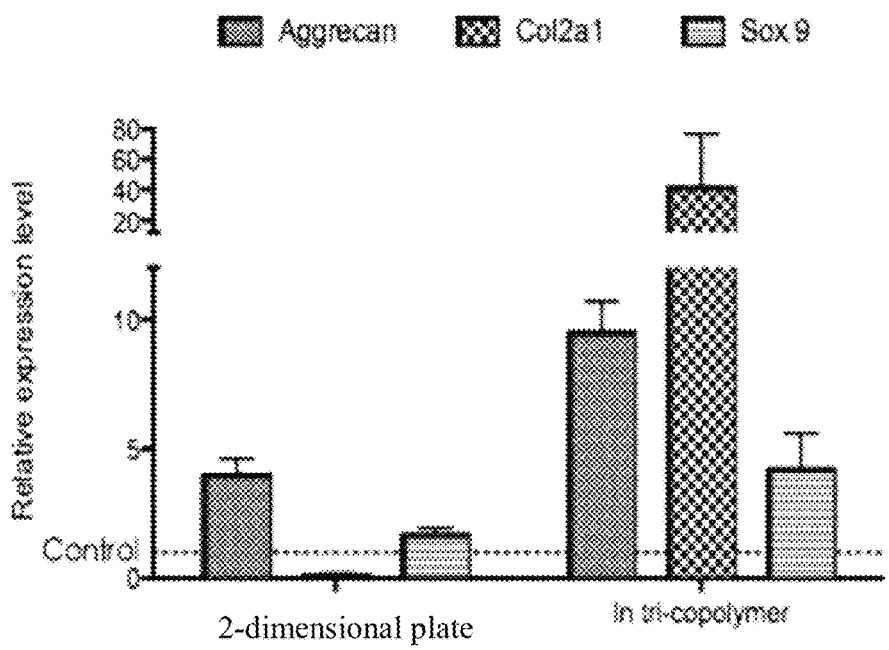
FIG. 10 shows the gene examination of the mesenchymal stem cell culturing on the 2-dimensional plate/scaffold for 7 days. Aggrecan, Col2a1 and Sox-9 have higher expression in the tri-copolymer culturing environment than in the 2-dimensional plate culture. The expression respectfully are: Aggrecan (9.49±1.22-fold), Col2a1 (41.52±35.52 times), and Sox-9 (4.20±1.40-fold); ($n=3*p <0.05***p<0.001$).

After cells seeded into the scaffold, the difference of gene expression was detected. At the static culture environment, the gene expressions of the 2-dimensional plate culture and the tri-copolymer culture at the presence of 1.0 kartogenin for 7 days of culture were compared. As shown in FIG. 10, Aggrecan, Col2a1 and Sox-9 have higher expression in the tri-copolymer culturing environment than in the 2-dimensional plate culture. The expression respectfully are: Aggrecan (9.49±1.22-fold), Col2a1 (41.52±35.52 times), and Sox-9 (4.20±1.40-fold). These results showed that except for kartogenin, the presence of tri-copolymer and kartogenin also had the effects for promoting chondrogenic differentiation.

Example 4

Differentiation of Coculture Construct of the Stem Cell and the Tri-Copolymer in the Bioreactor The fluorescent staining of Calcein-AM and Propidium Iodide (PI) was used to examine the survival distribution of the cells in the scaffold. The former was lipophilic which could easily enter into the living cell and being hydrolyzed to produce fluorescent compounds, calcein, so that only the living cell could be stained with Calcin-AM. The wavelengths of the absorption light and the emission light were 494/517 nm. Propidium Iodide was used to stain cell nucleus which could not enter into the living cell. When PI bound to a DNA double helix, it emitted red fluorescence. The wavelengths of the absorption light and the emission light were 535/617 nm.

Figure 11:
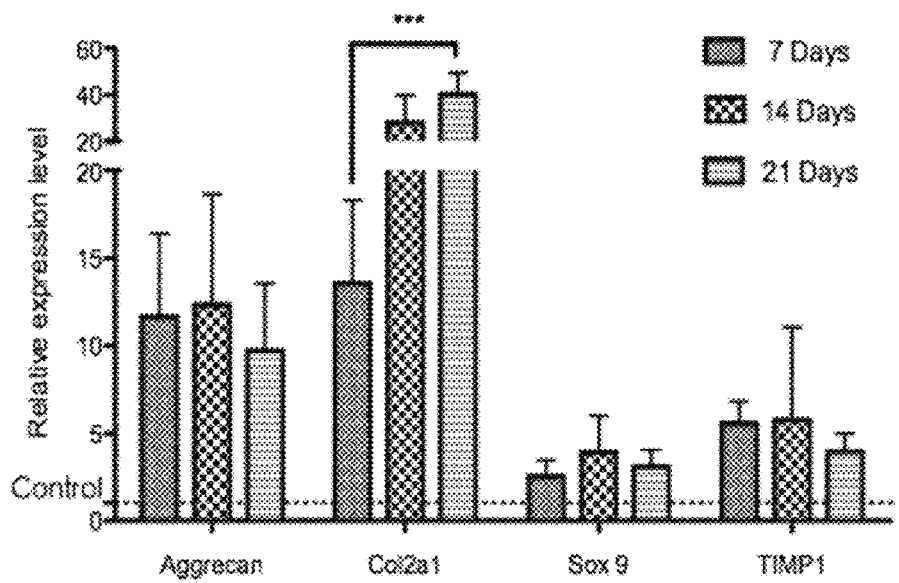
FIG. 11 shows the cartilage gene examination of the mesenchymal stem cell culturing in the bioreactor for 21 days. mRNA genes expression are examined under 7, 14 and 21 days of bioreactor culture. The cartilage genes Aggrecan, Col2a1 and Sox-9 are respectively examined; ($n=3*p<0.05***p<0.001$).

After culturing the tri-copolymer material, the mesenchymal stem cell and kartogenin in the bioreactor for 7, 14 and 21 days, mRNA genes expression were examined. The cartilage genes Aggrecan, Col2a1 and Sox-9 were examined respectively (as shown in FIG. 11). In this example, the control group was the mesenchymal stem cell culturing on the for 1 day.

The expressions of the initial regulation factor of chondrosis, Sox-9, at the three time points day 7, day 14, and day 21 were 2.51±0.90-fold, 3.91±2.12-fold, and 3.06±0.99-fold, respectively. There were no significant differences among the three time points, and all of them were up-regulated.

Compared to the control group, the expressions of the Aggrecan at the three time points day 7, day 14, and day 21 were 11.66±4.75-fold, 12.33±6.3-fold, and 9.74±3.83-fold, respectively. There were no significant differences among the three time points, and all of them were up-regulated.

Compared to the control group, the expressions of the Col2a1 gene at the three time points day 7, day 14, and day 21 were 13.6±4.7-fold, 28.26±11.64-fold, and 40.32±9.13-fold, respectively. After 7 days of culture it was up-regulated compared to the control group. After 21 days of culture, the expression had significant difference compared to the day 7.

The expression of TIMPs also was up-regulated during the 21 days of culture. The expressions at the three time points were 5.60±1.24-fold, 5.79±5.25-fold, and 3.94±1.08-fold, respectively.

Figure 12:
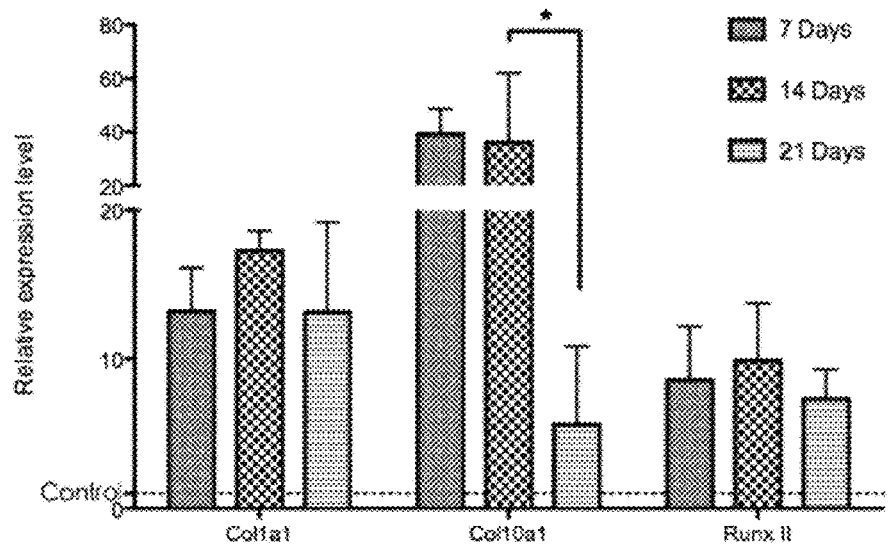
FIG. 12 shows the hypertrophic chondrocyte gene examination of the mesenchymal stem cell culturing in the bioreactor for 21 days. mRNA genes expression are examined under 7, 14 and 21 days of bioreactor culture. The hypertrophic chondrocyte genes, Col1a1, Col10a1 and Runx 2 are respectively examined; ($n=3*p<0.05***p<0.001$).

After culturing in the bioreactor for 7, 14, and 21 days, mRNA gene expression was examined. The hypertrophic chondrocyte genes, Col1a1, Col10a1 and Runx 2 were respectively examined (as shown in FIG. 12). In this example, the control group was the mesenchymal stem cell culturing on the 2-dimensional plate for 1 day.

The expressions of Col1a1 which was expressed lower in the cartilage, compared to the control group, at the three time points day 7, day 14, and day 21 were 13.19±2.90-fold, 17.26±1.38-fold, and 13.14±6.07-fold, respectively.

The expressions of Col10a1 which was initial chondrocyte hypertrophy characteristic gene at the three time points day 7, day 14, and day 21 were 39.23±9.39-fold, 36.08±26.00-fold, and 5.56±5.23-fold, respectively. After 7 days of culture, it was up-regulated compared to the control group. After 21 days of culture, the expression had significant difference compared to the day 14.

Generally, Runx 2 is the initial gene for chondrocytes developing into bone. Compared to the control group, at the three time points day 7, day 14, and day 21, the expressions of Runx 2 were 8.60±3.55-fold, 9.89±3.82-fold and 7.35±1.96-fold, respectively. There were no significant differences among the three time points, and all of them were up-regulated. The regulation of Runx 2 was regarded as the indicator for stable maintenance of the present chondrogenic differentiation composition culturing for 21 days.

The morphology of the cell inside the tri-copolymer scaffold was examined by scanning electron microscope (SEM) at 4 time points: Day 0, 7, 14, and 21. After removing from the medium at each time point, the samples were washed in PBS, immersed in 2.5% formaldehyde for 30 minutes for protein immobilization and then washed in PBS, immersed in 1% osmium tetroxide for lipid immobilization. After the samples were washed, the water was removed by series alcohol dehydration method (25%, 50%, 70%, 95%, 100%). The samples were then dehydrated with critical point drying and examined by scanning electron microscope.

Figure 13:
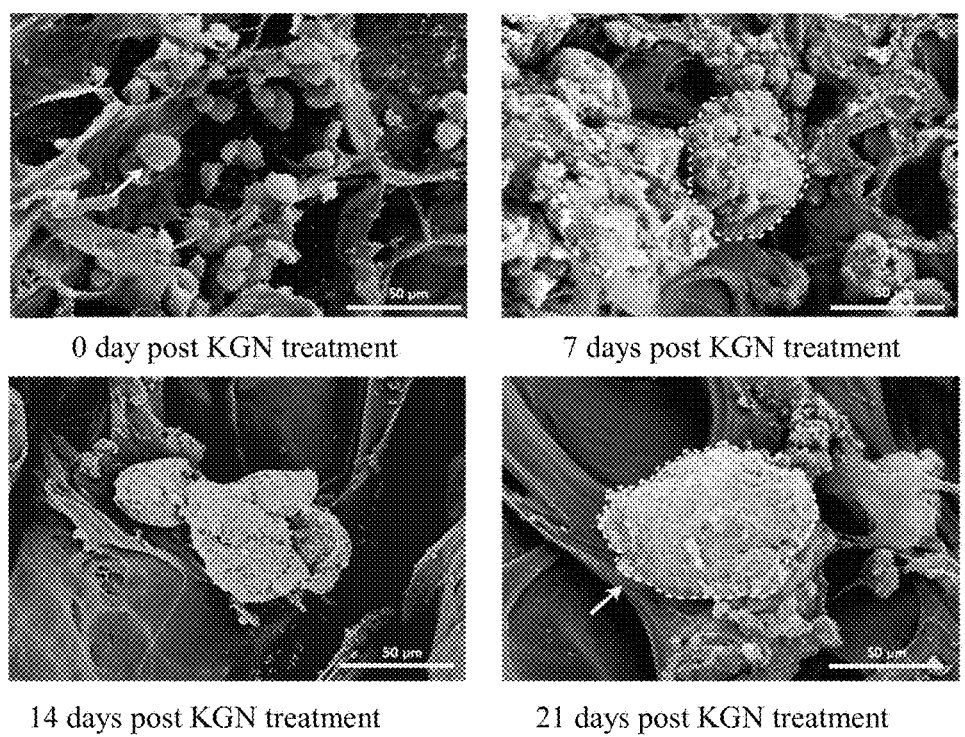
FIG. 13 shows the SEM examination of the mesenchymal stem cell culturing in the bioreactor for 21 days. The morphology of the cell inside the tri-copolymer scaffold is examined by scanning electron microscope (SEM); scale bar=50 μm.
Figure 14:
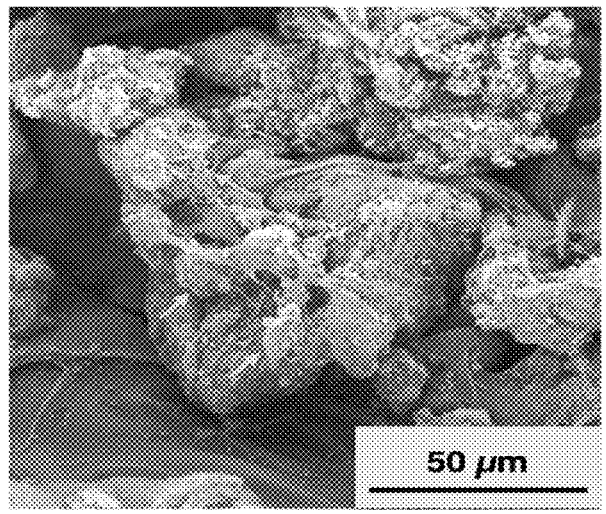
FIG. 14 shows the SEM examination of the mesenchymal stem cell culturing in the bioreactor for 7 days. During the 7 days of culture period, the attached cells (shown as the arrowhead) can still be distinguished from the surface of the cell mass; scale bar=50 μm.

As shown in FIG. 13, non-aggregated individual stem cells were distributed over the scaffold before the kartogenin added. The stem cells did not adhere to each other. The size of the single cell was about 10 µm. After adding kartogenin and culturing for 7 days, an aggregation of a cell mass was found in the SEM image, which the size was about 100 µm. After culturing for 14 days and 21 days, the size of the cell mass maintained in 100 µm and the diameter of the cell mass did not significantly increase. With the culturing process, the morphology of surface of the cell mass was different. As shown in FIG. 13, the surface of the cell mass was smoother at the day 21 which the cell mass secreted the extracellular matrix (ECM) and made the morphology of the cell surface change. However, during the 7 days of culture period, the attached cells (FIG. 14) can still be distinguished from the surface of the cell mass.

After combining the gelatin-hyaluronan-chondroitin tri-copolymer and the stem cell, the coculture construct was seeded and transferred into the dynamic bioreactor for culturing. The morphology of the differentiated cells were stained with Hematoxylin/Eosin, and in the present example, the cell-material complex sections were examined at 3 time points: Day 0, 7 and 21.

Figure 15:
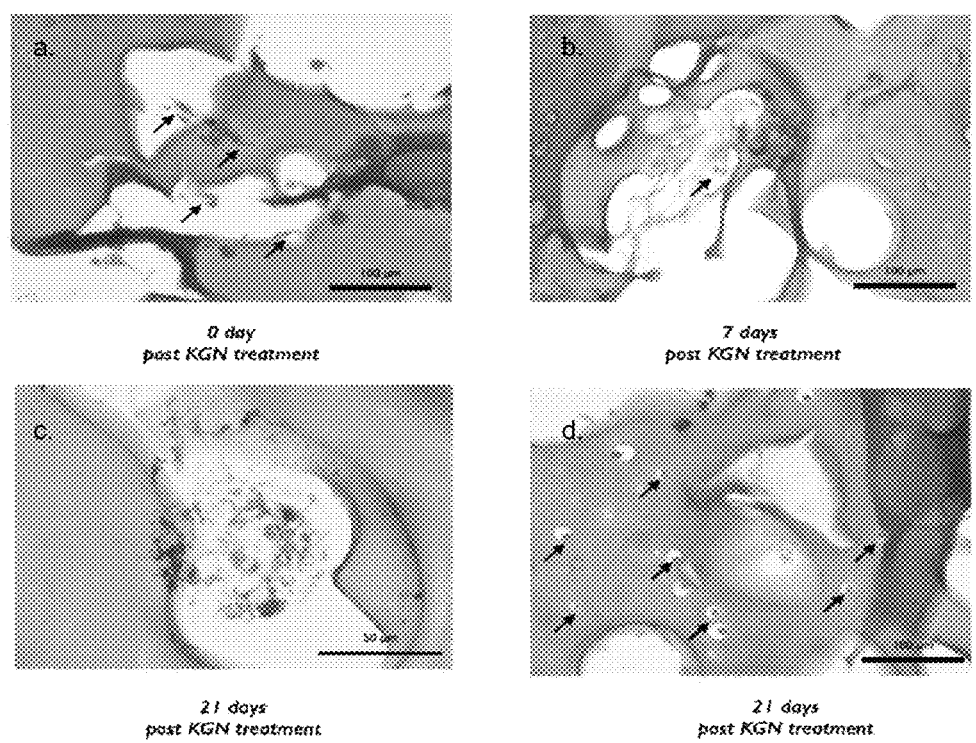
FIG. 15 shows the histological examination of the mesenchymal stem cell culturing in the bioreactor for 21 days. The cell-material complex sections are examined at 3 time points: Day 0, 7 and 21 which are (a) the distributed cells at the beginning of seeding, (b) cell condensation, (c) cell spheroid and (d) in the section of Day 21, lacunae like structure is examined; scale bar=50 μm.

As shown in FIG. 15(a), at early stage of culturing, the individual stem cells were distributed over the scaffold and the stem cells did not adhere to each other, the result was consistent with the SEM image. As shown in FIG. 15(b), the size of the single cell was about 10 µm. In the section of day 7, the aggregation of the cell mass was found and the histological results reflected that in kartogenin induction, cell condensation was presence as the same as culturing on the 2-dimensional plate.

In the section of day 21, the cell mass was examined, of which size was about 100 µm, as shown in FIG. 15(c). The cell in the cell mass was more aggregated than in the cell mass at day 7. In the section of day 21, lacunae like structure was examined which had one cell in the inner structure. The chondrocytes in the organism secreted lots of the extracellular matrix (ECM) and formed lacunae structure. In the present invention, the stem cells for chondrogenesis used the tri-copolymer material as matrix and drilled into lacunae like structure.

The aggrecan and the type II collagen were characteristic proteins of the cartilage cells. The coculture structure was cultured in the dynamic bioreactor and the expressions of the proteins were presented by immunohistochemical staining. The samples culturing under the dynamic culture environment for 7, 14, and 21 days were washed in PBS, immersed in 2.5% formaldehyde for 30 minutes for immobilization. The samples were paraffin-embedded and sectioned into 5 µm. The immunohistochemistry was used to examine the characteristic protein of the cartilage cells which comprises the aggrecan and the type II collagen. After dewaxing by xylene and rehydration, the activity of endogenous peroxidase was cleaned by Hydrogen Peroxide Block reagent (ab80436, abcam, MA, USA). After antigen was repaired, non-specific background protein was bound by Protein Block (ab80436). The primary antibodies (rabbit anti-collagen-II (ab53047), rabbit anti-aggrecan (GTX86902)) of type II collagen and aggrecan were reacted with the tissue slices at 4° C. for 12 hr. After rinsing, the slices were bound with horseradish peroxidase (HRP) conjugated secondary antibody (goat anti-rabbit HRP conjugate). Finally, Diaminobenzidine (DAB) reagent was reacted to the slices that showed the antigen expressing site. Last, the hematoxylin was incubated with the slices at room temperature for 30 minutes for counterstain.

Figure 16:
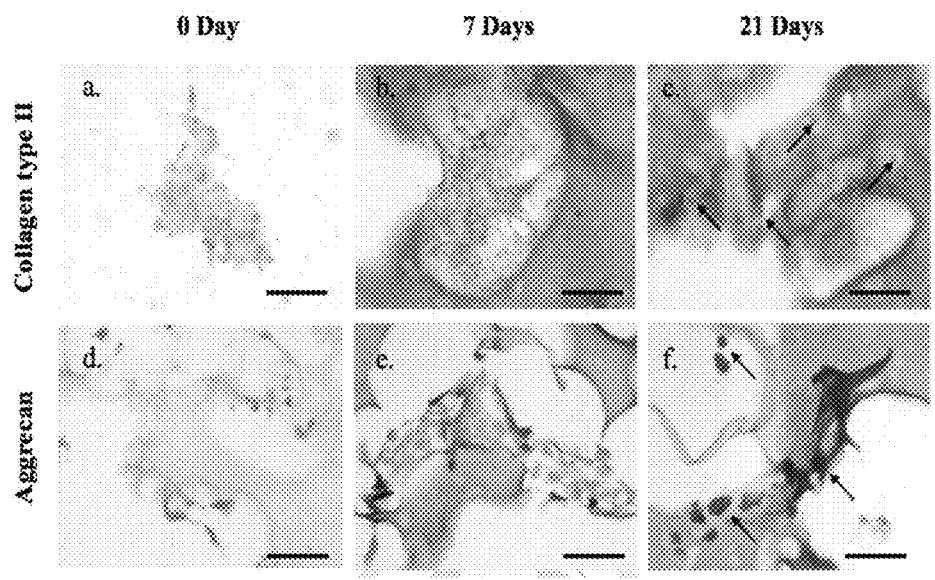
FIG. 16 shows the immunostaining examination of the mesenchymal stem cell culturing in the bioreactor. The chondrocyte characteristic protein Aggrecan and type II collagen are examined. Brown is for diaminobenzidine (DAB) and hematoxylin is for counter staining; scale bar=50 μm.

In the present example, the cell-material complex sections were examined at 3 time points: Day 0, 7 and 21. The staining results were shown in FIG. 16, which (a), (b), and (c) were type II collagen staining and (d), (e), and (f) were aggrecan staining The different number corresponded to the different time points.

At the beginning of the cell seeding (as shown in FIGS. 16(a) and (d)), the expressions of type II collagen and aggrecan were not distinct. These results showed that at the beginning of the cell culture, the chondrocyte characteristic proteins were not secreted. Reviewing the expression of type II collagen at day 7 and 21, both the tri-copolymer and the cell mass were positively stained. In the examination of day 7 staining, the cell mass could be reviewed by the counterstain of hematoxylin. Both the cell mass and the peripheral scaffold showed the accumulation of the type II collagen. The slice staining at day 21 showed that the lacunae structure was examined and the type II collagen was expressed on the peripheral of the structure.

As type II collagen was accumulated on the material, aggrecan was mainly expressed on the cell (as shown in FIGS. 17(e) and (f)) at day 7 and day 21. Compared between the two time points, the DAB staining at day 21 was darker and showed the higher expression of aggrecan.

Glycosaminoglycans (GAGs) were mainly the content of the extracellular matrix secreted by the chondrocyte. At day 21, Safranin-O staining showed the expression of GAGs through the Safranin-O fluorescence excitation.

Figure 17:
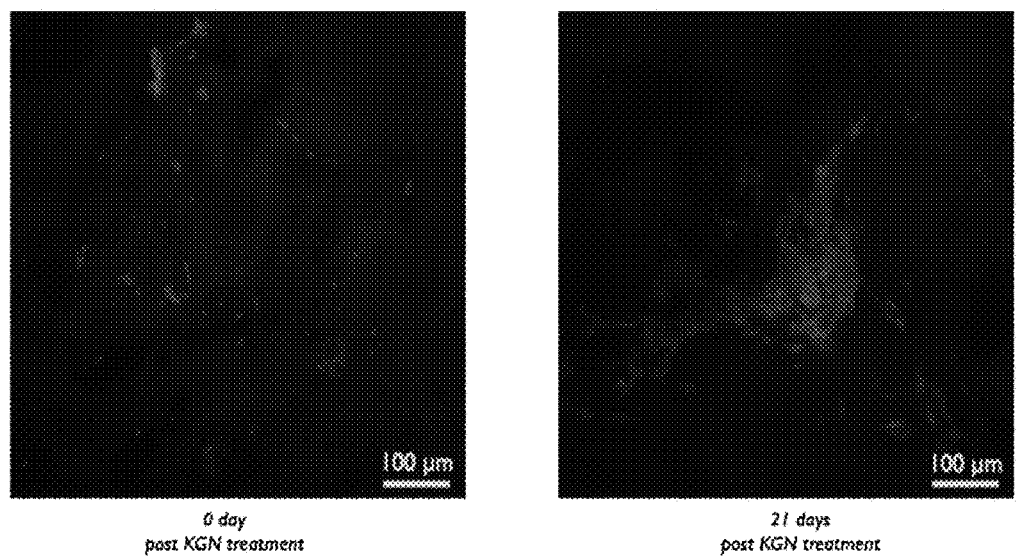
FIG. 17 shows the accumulation of glycosaminoglycans of the mesenchymal stem cell culturing in the bioreactor. The secretion of glycosaminoglycans is examined by Safranin-O staining which is displaying red for (a) Day 0 and (b) Day 21 of bioreactor culture. The cell nucleus is stained by Hochest and is displaying blue; scale bar=100 μm.

As shown in FIG. 17, the cell nucleus was stained by Hochest and displaying blue. The cells were distributed on the tri-copolymer scaffold at the beginning of culture. Red was for Safranin-O staining. The Safranin-O staining of the background was from the chondroitin-6-sulfate of the material itself which was one of the Glycosaminoglycans. This also showed that in the moist environment, the pore size of the scaffold was larger than the electron microscopy image which was in the drier environment. After the cell culturing for 21 days, the cell mass was examined, of which size was about 100 μm. The accumulation of the GAGs was examined on the surface of the cell mass.

1,9-dimethylmethlene blue (DMMB) method was used for quantifying Glycosaminoglycans (GAGs). 16 mg of DMMB was dissolved in 5 mL of 95% ethanol and diluted with 3 mL of formic acid and 25.6 mL of NaOH. Double distilled water was used to adjust the final volume to 1 liter, and the solution was maintained at pH 3.5.

250 μL of the DMMB solutions were added into 40 μL of the diluted sample solutions which were from different time points. After reacted in the dark for 10 min, the absorbance of 520 nm was detected and then the GAGs concentration was determined by interpolated onto the standard curve calculated by the chondroitin-6-sulfate.

Figure 18:
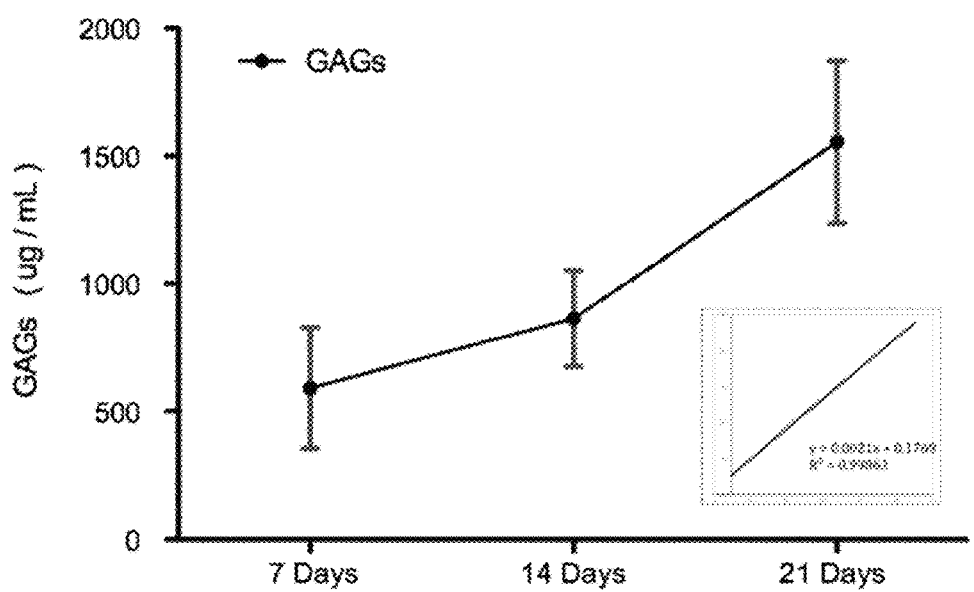
FIG. 18 shows the examination of glycosaminoglycans of the mesenchymal stem cell culturing in the bioreactor. 1,9-dimethylmethlene blue (DMMB) method is used to measure the glycosaminoglycans concentration in the medium at Day 7, 14 and 21. Calibration curve is established by chondroitin-6-sulfate.

The GAGs concentrations in the medium were determined by the DMMB method through collecting samples from the bioreactor at different time points. As shown in FIG. 18, with the culture time went, the secretion of the GAGs was also increased.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for promoting differentiation of a mesenchymal stem cell into cartilage tissue by using a culture medium and a bioreactor, the method consists of:
   (a) contacting the mesenchymal stem cell with a gelatin-hyaluronan-chondroitin tri-copolymer scaffold and a kartogenin in the culture medium; and
   (b) culturing the mesenchymal stem cell and the gelatin-hyaluronan-chondroitin tri-copolymer scaffold in the bioreactor,
   wherein the cartilage tissue comprises lacunae structure which is formed in vitro.

2. The method of claim 1, wherein concentration of the kartogenin is 0.03-2 µM.

3. The method of claim 1, wherein outer pore of the gelatin-hyaluronan-chondroitin tri-copolymer scaffold is smaller than inner pore of the scaffold.

4. The method of claim 1, which generates the cartilage tissue after 3-21 days of culture.

* * * * *